US007553478B2

(12) United States Patent
Madras et al.

(10) Patent No.: US 7,553,478 B2
(45) Date of Patent: Jun. 30, 2009

(54) METHODS FOR DIAGNOSING AND MONITORING TREATMENT ADHD BY ASSESSING THE DOPAMINE TRANSPORTER LEVEL

(75) Inventors: Bertha K. Madras, Newton, MA (US); Alan J. Fischman, Boston, MA (US); Peter C. Meltzer, Lexington, MA (US)

(73) Assignees: President and Fellows of Harvard College, Cambridge, MA (US); Organix, Inc., Woburn, MA (US)

(*) Notice: Subject to any disclaimer, the term of this patent is extended or adjusted under 35 U.S.C. 154(b) by 84 days.

(21) Appl. No.: 11/489,394

(22) Filed: Jul. 18, 2006

(65) Prior Publication Data
US 2006/0257316 A1 Nov. 16, 2006

Related U.S. Application Data

(63) Continuation of application No. 09/932,302, filed on Aug. 17, 2001, now Pat. No. 7,081,238, which is a continuation-in-part of application No. 09/605,621, filed on Jun. 28, 2000, now abandoned.

(60) Provisional application No. 60/141,540, filed on Jun. 28, 1999.

(51) Int. Cl.
*A61K 49/00* (2006.01)
(52) U.S. Cl. .............. 424/9.2; 424/1.11; 424/1.65; 424/1.81; 424/9.1
(58) Field of Classification Search ............... 424/1.11, 424/1.65, 1.81, 1.85, 1.89, 9.1, 9.2, 9.3, 9.4, 424/9.5, 9.6, 9.7, 9.8; 534/7, 10–14; 546/1, 546/4, 5, 10, 124, 132; 514/304
See application file for complete search history.

(56) References Cited

U.S. PATENT DOCUMENTS

| | | | |
|---|---|---|---|
| 3,813,404 A | | 5/1974 | Clarke et al. |
| 5,493,026 A | | 2/1996 | Elmaleh et al. |
| 5,496,953 A | | 3/1996 | Kuhar et al. |
| 5,500,343 A | | 3/1996 | Blum et al. |
| 5,621,133 A | | 4/1997 | DeNinno et al. |
| 5,747,523 A | * | 5/1998 | Jackson .............. 514/427 |
| 5,760,055 A | | 6/1998 | Davies |
| 5,770,180 A | | 6/1998 | Madras et al. |
| 5,874,090 A | | 2/1999 | Baker et al. |
| 5,902,797 A | | 5/1999 | Bell et al. |
| 5,948,933 A | * | 9/1999 | Meltzer et al. .............. 558/426 |
| 6,008,227 A | | 12/1999 | Davies et al. |
| 6,011,070 A | | 1/2000 | Froimowitz et al. |
| 6,171,576 B1 | * | 1/2001 | Meltzer et al. .............. 424/1.65 |
| 6,350,758 B1 | | 2/2002 | Kozikowski et al. |
| 6,353,105 B1 | * | 3/2002 | Meltzer et al. .............. 546/125 |
| 6,358,492 B1 | | 3/2002 | Kuhar et al. |
| 6,417,221 B1 | * | 7/2002 | Meltzer et al. .............. 514/432 |
| 6,531,483 B1 | | 3/2003 | Kuhar et al. |
| 6,548,041 B1 | * | 4/2003 | Meltzer et al. .............. 424/1.65 |
| 6,670,375 B2 | * | 12/2003 | Meltzer et al. .............. 514/304 |
| 7,081,238 B2 | * | 7/2006 | Madras et al. .............. 424/1.65 |
| 7,105,678 B2 | * | 9/2006 | Meltzer et al. .............. 546/132 |

FOREIGN PATENT DOCUMENTS

| | | |
|---|---|---|
| WO | WO 94/04146 | 3/1994 |
| WO | WO 97/16210 | 5/1997 |
| WO | WO 97/40859 | 11/1997 |
| WO | WO 98/24788 | 6/1998 |
| WO | WO 99/07359 | 2/1999 |

OTHER PUBLICATIONS

Madras et al (Dec. 1998), Synapse, vol. 29, No. 2, pp. 105-115.*
J.M. Swanson, et al., "Attention-deficit disorder and hyperkinetic disorder," Lancet, XX, XX vol. 351, No. 9100, Feb. 7, 1998, pp. 438-440, XP004265114.
K.H. Krause, et al., "Increased striatal dopamine transporter in adult patients with attention deficit disorder: effects of methylphenidate as measured by single photon emission computed topography," Neuroscience Letters, vol. 285, No. 2, May 12, 2000, pp. 107-110, XP002239034.
D. Dougherty, et al., "Dopamine transporter density in patients with attention deficit hyperactivity disorder," Lancet, XX, XX, vol. 354, No. 9196, Dec. 18, 1999, pp. 2132-2133, XP004263271.
I.D. Waldman, et al., "Association and Linkage of the dopamine transporter gene and attention-Deficit hyperactivity disorder in children: Heterogeneity owing to diagnostic subtype and severity," American Journal of Human Genetics, Dec. 1998, vol. 63, No. 6, pp. 1767-1776, XP-002239035, (Abstract).
A.J. Fischman, et al., "Rapid detection of Parkinson's disease by SPECT with altropane: a selective ligand for dopamine transporters," Synapse (New York, NY), Jun. 1998, vol. 29, No. 2, pp. 128-141, XP-002239036, (Abstract).
Ernst et al., "High Midbrain [1° F]DOPA Accumulation in Children With Attention Decificit H~eractivi Disorder", Am J Ps chiat, 156:8, Au', Vust 1999.
Ernst et al., "DOPA Decarboxylase Activity in Attention Deficit Hyperactivity Disorder Adults. A [Fluorine- 18]Fluorodopa Positron Emission Tomographic Study", The Journal of Neuroscience, Aug. 1, 1998, 18(15):5901-5907.
Arnold et al., "National Institute of Mental Health Collaborative Multimodal Treatment. Study of Children with ADHD (the MTA). Design Challenges and Choices," Arch. Gen. Psychiatry, 54(9):865-70(1997.

(Continued)

*Primary Examiner*—D. L. Jones
(74) *Attorney, Agent, or Firm*—Edwards Angell Palmer & Dodge LLP; George W. Neuner; Mark D. Russett

(57) ABSTRACT

A method of diagnosing attention deficient-hyperactivity disorder (ADHD) in a human patient by assessing the level of dopamine transporter in at least one region of the patient's central nervous system, where an elevated level of dopamine transporter in the patient is indicative of ADHD. In embodiments of the invention, assessment of dopamine transporter levels includes assessing binding of a dopamine transporter ligand to the dopamine transporters using PET or SPECT.

15 Claims, No Drawings

OTHER PUBLICATIONS

Babich et al., "C-11 Methyl-3p-[4-fluorophenyl]-N-iodo-E-allyl-IaH-5aH--nortropane-2(3carboxvlate: a hiehly selective DAT liaand for PET," J. Nuclear Medicine, 39:238 (1998).

Madras et al., "Imaging the Dopamine Transporter: A Window on Dopamine Neurons. Advances in Neurodegenerative Disorders," J. Marwah, H. Teitelbaum, Eds., vol. 1. Parkinson's Disease, pp. 229-253(1998).

Meltzer, et al., "Substituted 2-Phenyltropane Analogs of Cocaine; Synthesis, Inhibition of Binding at Cocaine Recognition Sites and Positron Emission Tomography (PET) Imaging," J. Med. Chem., 36:855-862(1993).

Sano et al., "A 40-Nucleotide Repeat Polymorphism in the Human Dopamine Transporter Gene," Hum. Genet., 91:405-406 (1993).

Seeman et al., "Anti-Hyperactivity Medication: Methylphenidate and Amphetamine," Mol.*Psychiatry*, 3(5):386-96 (1998).

Thapar et al., "Genetic Basis of Attention Deficit and Hyperactivity," Br. J. Psychiatry, 174:105-11 (1999).

Volkow et al., "Dopamine Transporter Occupancies in the Human Brian Induced by Therapeutic Doses of Oral Meth I whenidate," Am. J. *Psychiatry*, 155:1325-31 1998).

Waldman et al., "Association and Linkage of the Dopamine Transporter Gene and Attention-Deficit Hyperactivity Disorder in Children: Heterogeneity Owing to Diagnostic Subtype and Severity," Am. J. Hum. Genet, 639(6):1767-76 1998).

Wilens et al., "The Stimulants," Psychiatr. Clin North Am., 15(1):191-222 (1992).

Bonab et al., " Determination of Dopamine Transporter Density and Affinity Using High and Low *Specific Activity* In$^j$ections of C-11 Altro ane," J. Nuclear Medicine, 39:66 (1998).

Bonab et al., "Estimation of C-11-CFT Binding Potential by Iterative Fitting (IF) and Comparison with Reference Region Graphical (RRG) and Reference Fitting (RF) in Monkeys," J. Nuclear Medicine, 39:167 1998).

Canfield et al., "Autoradiographic Localization of Cocaine Binding Sites by [3H]CFT ([3H]WIN 35,428) in the *Monkey* Brain, " *Synapse*, 6(2):189-95 (1990).

Comings et al., "Polygenic Inheritance of Tourette Syndrome, Stuttering, Attention Deficit Hyperactivity, Conduct, and Oppositional Defiant Disorder: The Additive and Substractive Effect of the Three Dopaminergic Genes—DRD2, D beta H, and DAT1," Am. J. Med. Genet, 67(3):26488(1996).

Cook et al., "Association of Attention-Deficit Disorder and the Dopamine Transporter Gene," Am. J. Hum. Genet., 56(4):993-8 (1995).

Daly et al., "Mapping Susceptibility Loci in Attention Deficit Hyperactivity Disorder: Preferential Transmission of Parental Alleles at DAT1, DBH and DRD5 to Affected Children," Mol. Psychiatry, 4(2):192-6 1999).

Fischman et al., "SPECT Imaging of Dopamine Transporter Sites in Normal and MPTP-Treated Rhesus *Monkeys*," J. Nuclear Medicine, 38(1):144-50 1997.

Fischman et al., "Rapid Detection of Parkinson's Disease with Altropane, a SPECT Ligand," *Synapse*, 29:128-41 1998).

Gill et al., "Confirmation of Association Between Attention Deficit Hyperactivity Disorder and a *Dopamine Transporter Polymorphism*," Mol. *Psychiatry*, 2(4):311-3 (1997).

Greenhill et al., "Stimulant Medications," J. Am. Acad. Child Adolesc. Psychiatry, 38(5):503-12 (1999).

Kaufman et al., "Distribution of Cocaine Recognition Sites in Monkey Brain: 1. In Vitro Autoradio ra h with 3H CFT," *Synapse*, 9(3):177-87 (1991).

Kaufinan et al., "Distribution of Cocaine Recognition Sites in Monkey Brain: II. Ex Vivo Autoradio a h with 3H CFT and 125I RTI-55," *Synapse*, 12(2):99-111 (1992).

Madras et al., "Technepine: A High-Affinity 99m-Technetium Probe to Label the Dopamine *Transporter* in Brain b SPECT *Imaging*" *Synapse*, 22(3):239-46 (1996).

Madras et al., "N-Modified Fluorophenyltropane Analogs of Cocaine with High Affinity for Cocaine *Receptors*," Pharmacol. Biochem. Behav., 35(4):949-53 1990.

Madras et al., "Effects of Cocaine and Related Drugs in Nonhuman Primates. I. [3H]Cocaine *Binding* Sites in Caudate-Putamen," J. Pharmacol. *Ex p*. Ther., 251(1):131-41 (1989).

Madras et al., "['"I]Altropane, a SPECT Imaging Probe for Dopamine Neurons: I. Dopaine *Transporter Binding* in Nonhuman Primate Brain," *Synapse*, 29:93-104 1998).

Madras et al., "['"I]Altropane, a SPECT Imaging Probe for Dopamine Neurons: II. In Vitro and Ex Vivo Distribution in Primate Brain," *Synapse*, 29:105-115 (1998).

Madras et al., "[r'71]Altropane, a SPECT Imaging Probe for Dopamine Neurons: III. Human Dopamine Transporter in Post-Mortem Normal and Parkinson's Diseased Brain," Synapse, 29:116127(1998).

Krause et al., "Increased striatal dopamine transporter in adult patients with attention deficit hyperactivity disorder: effects of methylphenidate as measured by single photon emission computed tomog ach", Neuroscience Letters 285 (2000) 107-110.

Krause et al., Attention deficit hyperactivity disorder: binding of [$^{111}$Tc]TRODAT-1 to the dnnamine transnorter before and after methvnhenidate treatment.

Zametkins, M.D.; and Wendi Liotta "The Neurobiology of Attention-Deficit/Hyperactivity Disorder" J Clin Psychiatry 1998;59 (siuppl 7).

Biederman et al, "High Risk for attention Deficit Hyperactivity Disorder Among Children of Parents with Childhood Onset of the Disorder: A Pilot Study," Am. J. Psychiatry, 152(3)431-35 (1995).

Bertha K. Madras, et al., T*he Dopamine Transporter: Relevance To Attention Deficit Hyperactivity Disorder*(*ADHD*), Behavioural Brain Research, vol. 130 (2002) pp. 57-63.

* cited by examiner

METHODS FOR DIAGNOSING AND MONITORING TREATMENT ADHD BY ASSESSING THE DOPAMINE TRANSPORTER LEVEL

CROSS-REFERENCE TO RELATED APPLICATIONS

The present application is a continuation of U.S. application Ser. No. 09/932,302, filed Aug. 17, 2001, now U.S. Pat. No. 7,081,238; said U.S. application Ser. No. 09/932,302 is a continuation-in-part of U.S. application Ser. No. 09/605,621, filed on Jun. 28, 2000, now abandoned, which claims the benefit of provisional application No. 60/141,540, filed on Jun. 28, 1999. All of these applications are incorporated herein by reference.

FEDERALLY SPONSORED RESEARCH

This invention was made at least in part with government funding (NIH grants: DA06303, DA09462, NS30556, DA11558, and DA00304) and the government has certain rights in the inventions.

FIELD OF THE INVENTION

The present invention relates to the dopamine transporter, to imaging the dopamine transporter, and to diagnosing and monitoring ADHD.

BACKGROUND OF THE INVENTION

Attention Deficit Hyperactivity Disorder (ADHD) is characterized by heterogeneous problems with inattention, impulsivity, and hyperactivity. Mercugliano, 1999, *Pediatr. Clin. North Am.* 46:831-843; Faraone, et al., 1999, "The neurobiology of attention deficit hyperactivity disorder" in *Neurobiology of Mental Illness*, Charney, et al., eds., Oxford University Press, New York, pp. 788-801. It is one of the most commonly diagnosed behavioral disorders in children, affecting approximately 3-5% of school age children Faraone, et al., 1999, supra; 1998, "Diagnosis and Treatment of Attention Deficit Hyperactivity Disorder (ADHD)" *NIH Consensus Statement* 16:1-42. In addition, it is estimated that the majority of patients with ADHD will continue to have significant symptoms as adults. *NIH Consensus Statement*, supra. Adults with ADHD tend to have fewer problems with hyperactivity, but more problems with inattention and distractibility. Many patients have ADHD in conjunction with other psychiatric disorders (co-morbidities), including depression, anxiety, conduct disorders, oppositional disorder, obsessive compulsive disorder, and alcohol and/or substance abuse. Biederman, et al., 1993, *Am. J. Psychiatry* 150:1792-1798. The symptoms of inattention, impulsivity, and hyperactivity significantly interfere with school and job performance and social interactions affecting both peers and families. Faraone, et al., 1999, supra. ADHD is typically treated with stimulant medications, although there is considerable controversy regarding the long-term use of these medications in children. Mercugliano, 1999, supra; *NIH Consensus Statement*, supra; Spencer, et al., 1996, *J. Am. Acad. Child Adolesc. Psychiatry* 35:409-432 [see comments].

The diagnosis of ADHD has evolved over the past fifty years and the syndrome has become better characterized. Although the current diagnostic criteria described in Diagnostic and Statistical Manual of Mental Disorders-IV (DSM-IV) are generally accepted, the validity of the diagnosis in many children and adults has been questioned because the diagnosis is based on subjective clinical evaluations. Spencer, et al., 1994, *Harv. Rev. Psychiatry* 1:326-335. A reliable diagnosis of ADHD can be made by expert psychiatrists or psychologists using standardized structured interviews and neuro-psychiatric tests to adequately assess the patient and rule out confounding co-morbidities. However, the diagnosis may be less reliable when made by inadequately trained or inexperienced practitioners. In addition, it is estimated that at least 40% of adult patients with a probable diagnosis of ADHD do not meet strict DSM-IV criteria, largely because of the criterion that symptoms begin before seven years of age. Applegate, et al., 1997, *J. Am. Acad. Child Adolesc. Psychiatry* 36:1211-1221; Barkley, et al., 1997, *J. Am. Acad. Child Adolesc. Psychiatry* 36:1204-1210 [see comments]. Thus, it appears that the clinical diagnosis of ADHD results in both the over- and under-diagnosis of large numbers of patients. An independent and objective biological test to support the clinical diagnosis of ADHD would be beneficial. *NIH Consensus Statement*, supra. However, there has been doubt expressed by physicians that structural imaging studies, e.g., using single photon emission tomography (SPECT), would prove to be useful for the evaluation or management of ADHD. Zametkin, et al., 1998, *J. Clin. Psychiatry* 59 (suppl. 7): 17-23.

Attention deficit-hyperactivity disorder (ADHD) is a recognized syndrome characterized by a relatively high incidence in children with persistence into adulthood. Some research suggests that ADHD has a genetic component. Biederman et al., 1995, *Am. J. Psychiatry* 152(3):431-35; Arnold et al., 1997, *Arch. Gen. Psychiatry* 54:865-70. Paradoxically, stimulant drugs such as methylphenidate, d-amphetamine and pemoline are effective medications for treating ADHD in children and adults. Seeman and Madras, 1998, *Molecular Psychiatry* 3:385-96; Arnold et al., 1997, supra; Greenhill, et al., 1999, *J. Am. Acad. Child Adolesc. Psychiatry*, 38(5):503-12; Wilens, et al., 1992, *Psychiatric Clinics of N. Am.* 15(1): 191-222.

Increased recognition of the disorder has led to increased prescription of stimulant medications for treating ADHD. There is concern about the possibility of over-diagnosis of ADHD and resulting unnecessary treatment with stimulant drugs that have inherent potential for abuse. Conversely, if ADHD is underdiagnosed, patients who could be helped may go untreated. Thus, improved methods and products for diagnosis of ADHD and assessment of the effect of treatment of ADHD are desired.

SUMMARY OF THE INVENTION

We have recognized that the dopamine transporter (DAT) in the human brain is a useful protein for diagnosing and monitoring the course of ADHD. Although ADHD appears to result from multifactorial genetic, neurological, and environmental factors, recent data suggest that dysregulation of catecholamine transmitters, including dopamine and norepinephrine, in the brain may be the underlying mechanism of ADHD. There is additional evidence to suggest that dopamine transporters (DATs) are causally involved in the pathogenesis of ADHD. We have concluded that the involvement of DATs in ADHD is suggested by the fact that stimulant medications, such as methylphenidate (Ritalin™), pemoline (Cylert™), and dextroamphetamine (Adderall™, Dexadrine™), that are currently used to treat ADHD specifically target dopamine transporters in the brain. The involvement of DATs is also supported by genetic studies that demonstrate a genetic linkage between certain alleles of DAT genes and familial or hereditary forms of ADHD. Although the specific relationship of DATs to ADHD is still not understood, it is likely that over expression or altered function of DATs is associated with ADHD. Thus, an objective measurement of DATs in the brain can facilitate the diagnosis, assessment and investigation of the mechanism of ADHD.

Various dopamine transporter imaging agents can be used to assay the dopamine transporter as a biological marker for ADHD. Such imaging is used to diagnose ADHD and to monitor it, e.g. as the patient matures and/or is treated over time.

The present invention provides methods of diagnosing attention deficient-hyperactivity disorder (ADHD) in a human patient by assessing or determining dopamine transporter activity in at least one region of said patient's central nervous system.

The method preferably comprises administering to the patient a labeled dopamine transporter ligand and the assessment comprises determining the amount of labeled dopamine transporter ligand that is bound to dopamine transporter. The amount of labeled dopamine transporter ligand that is bound to dopamine transporter is compared with a control. An elevated level of dopamine transporter in said patient is indicative of ADHD. PET or SPECT imaging are particularly preferred assessment techniques. The dopamine transporter ligand comprises a compound that binds to the dopamine transporter. Examples of suitable ligands include ($^{11}$C)CFT (($^{11}$C)WIN 35,428), ($^{123}$I)Altropane™, and ($^{18}$F)CFT. Ligands, particularly suitable for use in PET, include [$^{11}$C]Altropane™. Ligands, particularly suitable for use in SPECT, include technetium-labeled phenyltropane probes, such as ($^{99m}$Tc)technepine™, O-1505, and similar compounds. Other examples of compounds useful in the methods of the present invention are described in U.S. Pat. Nos. 5,506,359, 5,770,180, 5,948,933 and 6,171,576, and in U.S. application Ser. No. 09/568,106 filed May 10, 2000, the disclosures of which are hereby incorporated by reference. The portion of the patient's central nervous system for assessment is preferably a portion of the human brain, e.g., the striatum.

Assessing dopamine transporter to determine dopamine transporter levels can include assessing dopamine transporter availability or binding potential. For example, in a method wherein dopamine transporter availability is assessed, dopamine transporter availability in a patient is compared with the dopamine transporter availability in a control, wherein a higher dopamine transporter availability in the patient is indicative of ADHD. Similarly, when dopamine transporter binding potential is measured the dopamine transporter binding potential in the patient is compared with the dopamine transporter binding potential in a control, and a higher dopamine transporter binding potential in the patient is indicative of ADHD.

The present invention also provides a method of determining the effectiveness of an ADHD treatment for a human patient. The method includes determining or assessing an initial dopamine transporter level in at least one region of the patient's central nervous system, treating the patient and, then, determining or assessing dopamine transporter level in the same region, e.g., after two or more weeks of treatment. The initial and subsequent dopamine transporter levels are then compared to determine or assess the effectiveness of treatment. A decrease in dopamine transporter levels indicates that the treatment is effective. In preferred methods, a labeled dopamine transporter ligand is administered to the patient before assessing the initial dopamine transporter level and, if necessary, also before assessing the subsequent dopamine transporter level. In this method, the assessment comprises determining the amount of labeled dopamine transporter ligand that is bound to dopamine transporter. The subsequent step of assessing dopamine transporter levels can be repeated more than one time, in order to follow the course of treatment, as necessary.

The treatment of ADHD can include, for example, administration of a pharmaceutical, such as methylphenidate, pemoline, or an amphetamine. The assessment of effectiveness can include imaging by PET or SPECT techniques.

The effectiveness of a treatment can be determined by assessing dopamine transporter availability before treatment, and comparing this value with the dopamine transporter availability in subsequent assessment steps. A lower dopamine transporter availability in the subsequent assessment indicates that the treatment is effective. Similarly, the binding potential can be used to assess dopamine transporter levels, where the dopamine transporter binding potential in the initial assessment is compared with the binding potential in the subsequent assessment and a lower dopamine transporter binding potential in subsequent assessments indicates that the treatment is effective.

The invention also provides a method of determining whether an individual has a heightened probability of having ADHD. The method includes assessing the level of dopamine transporter in at least one region of the patient's central nervous system and comparing the patient's dopamine transporter level to a predetermined normal dopamine transporter level. A higher than normal level is indicative of a heightened probability of having ADHD. A labeled dopamine transporter ligand is administered before the assessing step, and the assessment step comprises determining the amount of labeled dopamine transporter ligand that is bound to dopamine transporter.

The invention further provides a method of monitoring the progress of a treatment for ADHD in a human patient. The method includes determining or assessing the level of dopamine transporter in at least one region of the patient's central nervous system a plurality of times during the treatment. Comparing the results of dopamine transporter level in the same region of the brain at various times during treatment enables one to monitor the progress of treatment. In this method, preferably a labeled dopamine transporter ligand is administered to the patient and the dopamine transporter level is assessed by measuring the amount of labeled dopamine transporter ligand that is bound to dopamine transporter. The amount of bound labeled dopamine transporter ligand is measured by any method of imaging, preferably using PET or SPECT imaging.

The methods of the present invention can provide one or more of the following advantages. For example, assessing dopamine transporter levels allows an objective, biologically based diagnosis of ADHD. Diagnosis based on dopamine transporter levels can be used for patients of all ages and both sexes. The method of the present invention are useful in diagnosing ADHD in adults, as well as in children. Preferred imaging agents used to assess dopamine transporter levels, for example, ($^{123}$I)Altropane™, are safe and well tolerated by patients.

Other features and advantages of the invention will be apparent to those skilled in the arts from the following description of the preferred embodiments and from the claims.

As used herein, the term "dopamine transporter ligand" means a compound that binds to the dopamine transporter. Preferred compounds bind selectively to the dopamine transporter in preference to the seratonin transporter.

DETAILED DESCRIPTION OF THE INVENTION

We have discovered that abnormal levels of the dopamine transporter in human brain is indicative of ADHD. Assessing dopamine levels in the brain, therefore, can confirm a diagnosis of ADHD, or can assist in monitoring treatment of ADHD.

Dopamine Transporter Assessment Techniques

Assessing dopamine transporter levels can be performed by assessing dopamine transporter availability using, e.g., PET (positron emission tomography) or SPECT (single photon emission computed tomography). To measure dopamine transporter availability, a labeled probe that targets the transporter is introduced into the brain, e.g., intravenously, and PET or SPECT is performed. From the PET or SPECT images, the density of the dopamine transporter is quantified by measuring the binding potential, where binding potential is defined as the maximum number of binding sites, $B_{max}$, divided by a dissociation constant, $K_d$, where $K_d$ is related to affinity.

Imaging agents that target the dopamine transporter include ($^{11}$C)Altropane™, ($^{11}$C or $^{18}$F)WIN 35,428(($^{11}$C)CFT), ($^{123}$I)Altropane™, ($^{99m}$Tc)O-1505, ($^{99m}$Tc)technepine™, and similar compounds. These agents bind the dopamine transporter with varying affinities, allowing multiple, dissimilar assessments to be performed. Structures, synthesis, and/or sources of some of the above agents are described in, e.g., Fischman et al., 1998, *Synapse* 29:125-41 (($^{123}$I)Altropane™); Madras et al., 1996, *Synapse* 22:239-46; Meltzer et al., 1993, *J. Med. Chem.* 36:855-62; and Milius et al., 1990, *J. Medicinal Chem.* 34:1728-31, each of which is incorporated herein by reference. Another useful compound includes $^{123}$I Ioflupane (DatSCAN) from Nycomed-Amersham.

Compounds that are useful as imaging agents in the methods of the present invention includes compounds described in pending application U.S. Ser. No. 09/568,106. These compounds have a tropane compound linked through the N atom at the 8-position to a chelating ligand capable of complexing a technetium or rhenium radionuclide to produce a neutral labeled complex that selectively binds to the dopamine transporter. The tropane compounds bind to the dopamine transporter. These compounds are represented by the following structural formula (II):

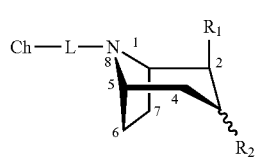

II wherein $R_1$ is α or β and is selected from COOR$^a$, COR$^a$, and CON(CH$_3$)OR$^a$;

$R_2$ is α or β and is selected from C$_6$H$_4$X, C$_6$H$_3$XY, C$_{10}$H$_7$X, and C$_{10}$H$_6$XY;

R$^a$ is selected from C$_1$-C$_5$ alky, e.g. methyl, ethyl, propyl, isopropyl, etc.;

X and Y are independently selected from R$^a$, H, Br, Cl, I, F, OH, and OCH$_3$;

L is —(CH$_2$)$_n$— where n is an integer from 1 to 6, or —(CH$_2$)$_n$-(aryl, arylalkyl, ethenyl or ethynyl)-(CH$_2$)$_m$— where the sum of n plus m is an integer from 1 to 6; and Ch is a tridentate or tetradentate chelating ligand that forms a neutral complex with technetium or rhenium.

$R_1$ and $R_2$ can be in the α or β configuration. Further, $R_1$ preferably can be substituted at the C$_2$ or C$_4$ when the tropane has a 1R or 1S configuration, respectively.

Any tropane compound of the general formula II is useful in the present invention so long as it binds to DAT. Examples of particularly useful tropanes are: 2-carbomethoxy-3-(4-fluorophenyl)-N-methyltropane ("WIN 35,428") (Clarke, R. L., et al., *J. Med. Chem.* 1973, 16, 1260-1267) which binds potently (IC$_{50}$=11.0 nM) and with specificity to the DAT (Meltzer, P. C., et al., *J. Med. Chem.* 1993, 36, 855-862); 2-carbomethoxy-3-(3,4-dichlorophenyl)-N-methyltropane ("O-401"; IC$_{50}$=1.09 nM) (Meltzer, P. C., et al., *J. Med. Chem.* 1993, 36, 855-862). Tropane analogs that have a 3α-group are of the boat configuration. Other tropanes having a 3β-oriented group are of the chair configuration.

Chelating ligands include any tridentate or tetradentate ligand that binds technetium or rhenium to form a neutral complex. The chelating ligand is covalently attached to the linker L, as described below. Preferred chelating ligands contain a plurality of N or S atoms for complexing with the radionuclide.

Examples of suitable ligands are the N$_2$S$_2$ compounds represented by the following structural formulas:

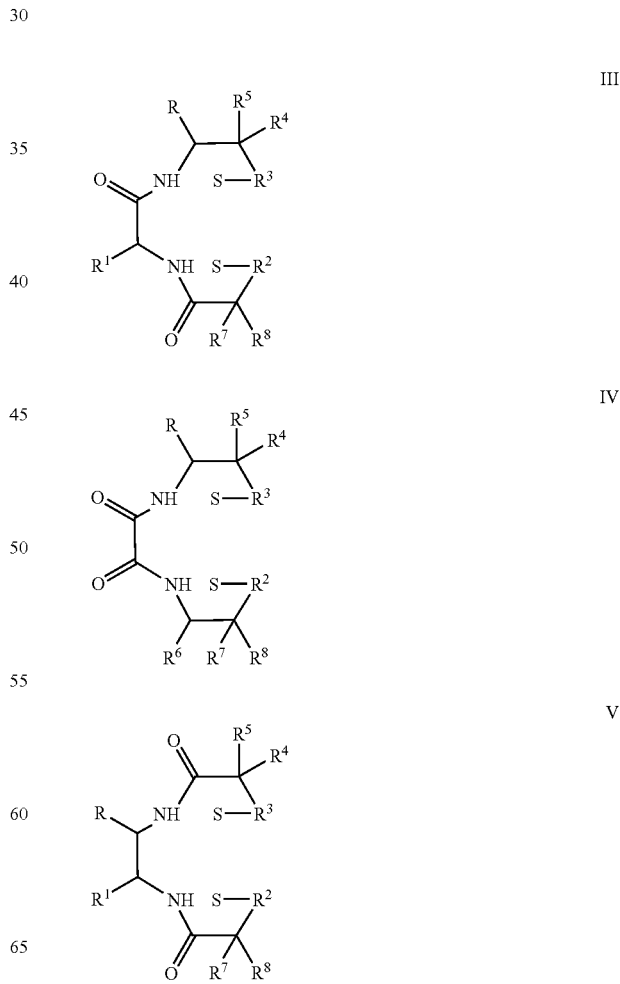

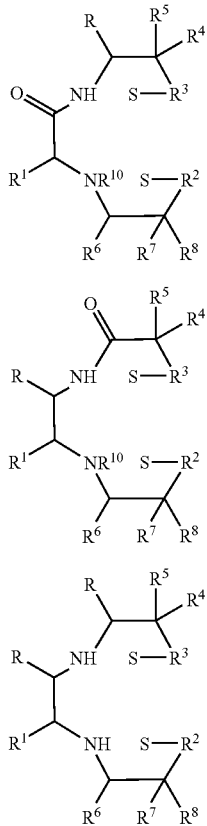

VI

VII

VIII wherein R, $R^6$, and $R^{10}$ are each selected from hydrogen, substituted or unsubstituted lower alkyl, alkyl$R^9$, or —$COR^9$ where $R^9$ is selected from hydroxy, substituted lower alkoxy, substituted or unsubstituted amino, glycine ester, halide (chloro, bromo, iodo) or OR (OR is a leaving group such as mesylate, triflate, or tosylate) or an activated leaving group; $R^1$ is selected from hydrogen, or substituted or unsubstituted lower alkyl; $R^2$ and $R^3$ are each selected from hydrogen or a thiol protecting group, or an inter or intramolecular disulfide; and $R^4$, $R^5$, $R^7$ and $R^8$ are each selected from hydrogen or lower alkyl.

When R, $R^6$ or $R^{10}$ is a carboxylic acid derivative, $R^9$ can be an activated leaving group. For purposes of this invention the leaving group $R^9$ is defined such that (compound) —$COR^9$ is an acylating agent. Examples of activated leaving groups suitable for the practice of this invention include, for example: halide; substituted or unsubstituted aryloxy groups such as phenoxy, pentachlorophenoxy, etc.,; oxy-heterocyclic groups such as N-oxy-succinimido, etc.; mercapto; lower alkylthio; arylthio; oxyphosphonium; and other groups known to those skilled in the art to be useful as leaving groups.

$R^2$ and $R^3$ can be hydrogen or any known thiol protecting group. Examples of such groups include lower alkylaminocarbonyl such as ethylaminocarbonyl, lower alkanoylaminomethyl, aroylaminomethyl, t-butyl, acetamidomethyl, arylmethyl such as triphenylmethyl (trityl) and diphenylmethyl, aroyl such as benzoyl, aryloxycarbonyl such as phenoxycarbonyl, aryloweralkoxycarbonyl, preferably arylmethoxycarbonyl, benzyloxycarbonyl, and lower alkoxycarbonyl such as t-butoxycarbonyl. Preferred thiol protecting groups include trityl, t-butyl, diphenylmethyl, acetamidomethyl and benzoyl and an inter or intramolecular disulfide.

The term "lower alkyl" when used herein designates aliphatic saturated branched or straight chain hydrocarbon monovalent substituents containing from 1 to 6 carbon atoms such as methyl, ethyl, isopropyl, n-propyl, n-butyl, etc., more preferably 1 to 4 carbons. The term "lower alkoxy" designates lower alkoxy substituents containing from 1 to 6 carbon atoms such as methoxy, ethoxy, isopropoxy, etc., more preferably 1 to 4 carbon atoms.

The terms substituted lower alkyl or substituted lower alkoxy when used herein include alkyl and alkoxy groups substituted with halide, hydroxy, carboxylic acid, or carboxamide groups, etc. such as, for example, —$CH_2OH$, —$CH_2CH_2COOH$, —$CH_2CONH_2$, —$OCH_2CH_2OH$, —$OCH_2COOH$, —$OCH_2CH_2CONH_2$, etc.

The term substituted amino when used herein includes such groups mono or di and tri-substituted with lower alky, and —$NH_3+$ or mono, di and tri-substituted ammonium groups substituted with lower alkyl with a pharmacologically suitable anion.

The term glycine ester as used herein means the lower alkyl esters of glycine, preferably the methyl and ethyl esters.

These chelating ligands can be complexed with a radionuclide, e.g., technetium, to form the following complexes:

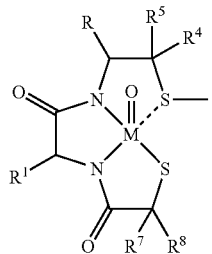

XI

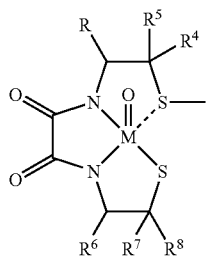

X

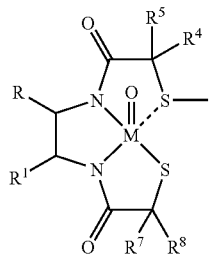

XI

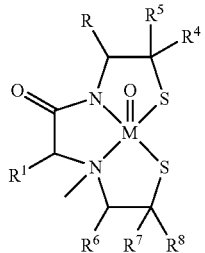

XII

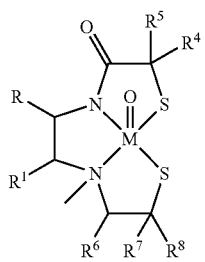

XIII

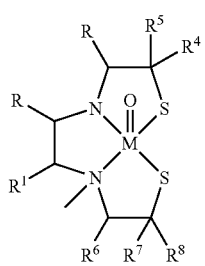

XIV where the R groups are defined as above.

These compounds use chelating ligands that are formed from monoaminomonoamide compounds having structures of formula V, VI or VII, e.g., N-{2-((2-((triphenylmethyl)-thio)-ethyl)amino)acetyl}-S-(triphenylmethyl)-2-aminoethanethiol ("MAMA'"). Any organic linker having a backbone chain length of 1 to about 6 carbon atoms can be used to attach the chelating ligand, typically through its nitrogen, sulfur, R, $R^1$ or $R^6$, to the 8-nitrogen atom of the tropane ligand (which binds the dopamine transporter). Examples of linkers include —$(CH_2)_n$— where n is an integer from 1 to 6, or —$(CH_2)_n$-(aryl, arylalkyl, ethenyl or ethynyl)-$(CH_2)_m$ where the sum of n plus m is an integer from 1 to 6.

An example of a compound having the above structure includes Technepine™, (O-861), which comprises a tropane, 2-carbomethoxy-3-(4-fluorophenyl)-N-methyltropane, also known as WIN 35,428, joined at the N-position to the MAMA' complexing ligand.

As mentioned above, another useful imaging agent is Altropane™. This and related compounds are described in U.S. Pat. No. 5,493,026 and include compounds having the following formula:

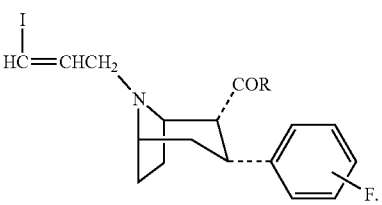

wherein the following condition is imposed on that formula:

R is —$CH_3$, —$CH_2CH_3$ (α configuration; β configuration or both), —$CH(CH_3)_2$, —$(CH_2)_nCH_3$, —$(CH_2)_nC_6H_4X$, —$C_6H_4X$, —$C_6H_5$, —$OCH_3$, —$OCH_3CH_2$, —$OCH(CH_3)_2$, —$OC_6H_5$, —$OC_6H_4X$, —$O(CH_2)_nC_6H_4X$, or —$(CH_2)_nCH_3$; wherein X is —Br, —Cl, —I, —F, —OH, —$OCH_3$, —$CF_3$, —$NO_2$, —$NH_2$, —CN, —$NHCOCH_3$, —$N(CH_3)_2$, —$(CH_2)_nCH_3$, $CHOCH_3$, or —$C(CH_3)_3$ and n is between 0 and 6 inclusive.

Other compounds can have the same formula, except that the substituent on the N-allyl group can be any halogen, preferably —I or —F. Other useful compounds are characterized as follows: a) the 2 substituent is in the β position; b) the 3 substituent is in the β position; c) R is —O—$CH_3$; the 8 substituent is either the E isomer or the Z isomer. More preferably the halo substituent on the N-allyl moiety is —I or —Br (particularly a radionuclide of —I or —Br); $^{18}F$ provides also a useful label. Most preferably, the compound is Iodoaltropane: 2-β-carbomethoxy-3-β-(4-fluorophenyl)-8-(3E-iodopropen-2-yl) nortropane. The compounds used in the present methods contain a radioactive label (particularly a gamma or position emitter such as $^{123}I$, $^{125}I$ $^{18}F$ or $^{11}C^{123}I$ is particularly preferred) or a $^{18}F$ fluoro label as part of the 3-halopropen-2-yl substituent.

Other techniques to identify anomalies in brains of ADHD patients include SPECT imaging to measure blood flow and functional MRI to measure regional metabolic function. Both techniques can demonstrate abnormal function of the frontal cortex.

Applications of Dopamine Transporter Assessments

Traditionally, ADHD is diagnosed by assessing a patient's cognitive and attentional skills. For example, according to the Diagnostic and Statistical Manual of Mental Disorders, 4th edition (DSM-IV), evidence of either inattention or hyperactivity and impulsivity are required to support a diagnosis of ADHD. Under the DSM-IV standard, a finding of inattention must be supported by six or more of the following symptoms, persisting for at least six months to a degree that is maladaptive and inconsistent with the patient's level of development: (1) fails to give close attention to details; (2) has difficulty sustaining attention to activities; (3) does not listen when spoken to directly; (4) does not follow through on instructions; (5) has difficulty organizing tasks; (6) avoids engaging in tasks that require sustained mental effort; (7) loses things necessary for activities; (8) is easily distracted by extraneous stimuli; (9) is forgetful in daily activities. Similarly, under the DSM-IV standard, a finding of hyperactivity and impulsivity must be supported by six or more of the following symptoms, persisting for at least six months to a degree that is maladaptive and inconsistent with the patient's level of development: (1) is fidgety; (2) leaves seat when expected to remain seated; (3) runs about in situations in which it is inappropriate; (4) has difficulty playing quietly; (5) acts as if "driven by a motor"; (6) talks excessively; (7) blurts out answers before questions have been completed; (8) has difficulty taking turns; (9) interrupts or intrudes on others. When used to diagnose ADHD in adults, the above criteria are modified slightly to apply to adult environments.

Diagnosis of ADHD using the DSM-IV standard is inherently somewhat subjective, leading to inconsistent diagnosis.

Assessment of dopamine transporter levels can complement, and in some cases, supplant, traditional ADHD diagnostic techniques. The dopamine transporter level assessments using PET or SPECT provide objective, biological criteria for diagnosing ADHD, and can be used, e.g., to confirm an ADHD diagnosis under the DSM-IV standard, to resolve conflicting diagnoses or to call into question a diagnosis or non-diagnosis of ADHD. Dopamine transport assessments can also be used to refine subjective testing criteria for ADHD.

In addition, PET and SPECT imaging of the dopamine transporter can be used to monitor and adjust treatment of ADHD. For example, methylphenidate, a drug commonly used to treat ADHD, may occupy the dopamine transporter. Volkow et al., 1998, *Am. J. Psychiatry* 155:1325-31. The effectiveness of methylphenidate treatment for a particular patient could be monitored by assessing dopamine transporter levels both before and after administration of methylphenidate. For example, dopamine transporter levels can be assessed immediately before a treatment, and then, e.g., two weeks, months, or longer after administration of treatment. If the methylphenidate successfully occupies dopamine transporters, it will displace the radio-labeled probe, decreasing the availability of dopamine transporter. The decreased availability of dopamine transporter will manifest as decreased binding potential in the PET or SPECT images. Such objective data can assist a physician in determining the most effective drug and the most effective dosage for a particular patient.

Dopamine transporter level assessments can also be used to monitor treatment over the long term, and to help a physician and patient determine whether treatment affects transporter levels and whether treatment can be stopped.

Finally, dopamine transporter level assessments can identify individuals at risk for ADHD. Patients found to have elevated dopamine transporter levels can, e.g., be referred for conventional ADHD testing.

Experimental Studies

Experimental data confirm the efficacy of diagnosing ADHD by detecting elevated dopamine transporter levels.

EXAMPLE 1

SPECT imaging of the dopamine transporter with [$^{123}$I]Altropane™ was conducted on six subjects previously diagnosed with ADHD, and on control individuals without a diagnosis of ADHD. Altropane™, E-2β-carbomethoxy-3β-(4-fluorophenyl)-N-1(1-iodoprop-1-en-3-yl)nortropane, is an iodo analog of N-allyl CFT (WIN 35,428), a phenyltropane analog. The molecular formula of Altropane™ is $C_{18}H_{21}NO_2F$. Before administration to human subjects or patients, Altropane™ was labeled with ($^{123}$I), a gamma-emitting isotope with a half-life of 13.2 hours. For each individual tested, greater than 1 mCi of ($^{123}$I)Altropane™ was administered by intravenous injection at the onset of imaging. Images of the striatum were collected and analyzed by a radiologist to determine striatal binding potentials. In general, the methodology used for the SPECT imaging was the same as the methods described in Fischman et al., 1998, *Synapse* 29:125-41, which is incorporated herein by reference.

The results of the imaging of ADHD patients are summarized below in Table 1:

TABLE 1

| | ADHD Patients | |
|---|---|---|
| INDIVIDUAL | AGE | BINDING POTENTIAL |
| ADHD-1 | 34 | 2.98 |
| ADHD-2 | 45 | 2.34 |
| ADHD-3 | 24 | 2.71 |
| ADHD-4 | 53 | 2.33 |
| ADHD-5 | 51 | 2.16 |
| ADHD-6 | 41 | 3.51 |
| MEAN | 41 | 2.67 |

These six ADHD individuals show elevated binding potential, and, therefore, elevated dopamine transporter levels compared to expected levels for aged matched normal individuals, which may range, generally, between about 1.0 and 2.2.

EXAMPLE 2

Pre-clinical in vivo and in vitro studies performed in monkeys demonstrated that Altropane™ preferentially binds to dopamine rich areas of the striatum with a density that is within the range reported for the dopamine transporter. Madras, et al., 1998, *Synapse* 29:105-115. Altropane™ has demonstrated high selectivity for the dopamine transporter, compared to the seratonin transporter. Madras, et al., 1998, *Synapse* 29:93-104. Further, in vitro binding studies demonstrated that Altropane™ binds to a specific high-affinity site on the dopamine transporter. Elmaleh, et al., 1996, *J. Nucl. Med.* 37:1197-1202; Madras, et al., 1998, *Synapse* 29:116-127.

The overall objective of this study was to confirm the results of a preliminary study and to further define the safety profile along with the sensitivity and specificity of ($^{123}$I)-Altropane™ SPECT binding potentials in the diagnosis of adult patients with ADHD, as compared to healthy volunteers without ADHD. The truth ("gold") standard is the clinical diagnosis of ADHD made by an expert psychiatrist/psychologist using structured diagnostic interviews and neuro-psychiatric testing, along with strict DSM-IV criteria for the diagnosis of ADHD, as described by Biederman and colleagues. Biederman, et al. 1993, supra.

Diagnostic Assessments:

Each underwent a standardized clinical assessment, as described by Biederman, et al., that included psychiatric evaluation, structured diagnostic interview, cognitive testing and neuropsychological battery, medical history and laboratory assessment. The clinical evaluation was conducted by a clinician who knows and treats adult ADHD.

Structured Diagnostic Interview:
  1) Structured Clinical Interview for DSM-IV (SCID) Adult DSM-IV Disorders
  2) Kiddie-Schedule for Affective Disorders and Schizophrenia (K-SADS-E) addition Childhood DSM-IV Disorders Neuropsychological Battery
  1) KBIT, WRAT-3 (Measures verbal, performance and freedom from distractibility IQ. This assessment is measured at baseline only.)
  2) Rey-Osterrieth Complex Figure (Measures planning and organization).

3) Conners Continuous Performance Tests (Auditory and Visual), (Measures sustained attention, selective attention and susceptibility to interference)
4) Stroop (Measures susceptibility to interference)

Rating Scales
1) Clinical Global Impression (CGI) Scale (NIMH, 1985).
2) The ADHD Symptom Checklist Severity Scale. DuPaul, 1991, *J. Clin. Child. Psychol.* 20:245-253; Murphy, et al., 1996, *Journal of Attention Disorders* 1:147-161.
3) The Hamilton Depression Scale (the 21-item Hamilton Depression Scale (HAM-D) will be completed by the physician to evaluate depressive symptoms). Hamilton, 1960, *Journal of Neurological and Neurosurgical Psychiatry* 23:56-62.
4) The Hamilton Anxiety Scale (the 14-item Hamilton Anxiety Scale will be completed by the Physician to evaluate symptoms of anxiety). Hamilton, 1959, *Br. J. Med. Psychol.* 32:50-55.
5) Beck's Depression Inventory (The 21-item Beck's Depression Inventory (BDI) will be completed by the physician to evaluate depressive symptoms). Beck, et al., 1961, *Arch. Gen.Psychiatry* 4:561-571.

SPECT Imaging with [$^{123}$I]-Altropane™:

Subjects were given SSKI or Lugol's solution treatment to decrease thyroid exposure to $^{123}$I. The dose was 5 drops PO once daily, beginning 24 hours before imaging, the day of imaging, and an additional 1 to 3 days after injection, per the discretion of the investigator. The total daily dose of SSKI or Lugol's should be 5 drops.

Procedures:
1) Perform pre-injection Brief Neurological Assessment
2) Position the subject in the scanner with appropriate head immobilization.
3) Administer radiopharmaceutical over approximately thirty (30) seconds, followed by a 20 mL saline flush administered over approximately thirty (30) seconds, such that the total infusion time for the Altropane™ plus the saline flush is approximately sixty (60) seconds
4) Acquire a series of consecutive two-minute SPECT scans.
5) Perform post-injection Brief Neurological Assessment approximately 60 to 90 minutes after [$^{123}$I]-Altropane™ administration.

($^{123}$I)-Altropane Administration and SPECT Imaging

Approximately 8 mCi [$^{123}$I]-Altropane™ was infused intravenously over approximately thirty (30) seconds, followed by a saline flush of 20 mL administered over approximately thirty (30) seconds, such that the total time of administration of the Altropane™ and saline flush was approximately sixty (60) seconds. (Note: Volume for an 8 mCi injection can vary from approximately 5 to 20 ml.)

Each clinical dose of a sterile, pyrogen-free solution of [$^{123}$I]-Altropane for intravenous (i.v.) injection contained:

| ($^{123}$I)-Altropane ™ | 8 mCi [$^{123}$I]~15 ng Altropane ™ |
|---|---|
| Ethanol, U.S.P. | 7% by volume |
| 0.9% Sodium Chloride for Injection, U.S.P. | 90% by volume |
| Water for Injection, U.S.P. | 3% by volume |

Effective head immobilization is very important for successful imaging. The orbital meatal line was aligned with the plane of rotation. Dynamic SPECT imaging was begun immediately after completion of the infusion. Approximately fifteen (15) SPECT studies were acquired in sequence, starting immediately after the completion of [$^{123}$I]-Altropane™ infusion. Each of the SPECT studies were acquired over a 2-minute period for a total of 60 minutes of imaging time, accounting for reset periods between each SPECT study.

A transverse slice set from each of the 15 SPECT studies was reconstructed using a Butterworth filter of order 4.0 and cut-off of 0.26 cycles/pixel as suggested starting points, or equivalent. (Note: images should be optimized for each gamma camera used.) Attenuation correction was performed using the Chang Algorithm.

Primary Analyses

A comparison was made between the ADHD and non-ADHD subjects with respect to baseline demographic and medical history data. For the quantitative variables the comparison used either a t-test or the Wilcoxon rank sum test, as appropriate. For the qualitative variables the comparison was based on Fisher's exact test.

Quantitative Analysis of [$^{123}$I]-Altropane Images

An estimate of the striatal binding potential of [$^{123}$I]-Altropane™ (k3/k4) was calculated by the reference region approach as described by Farde, et al. to quantify [$^{11}$C]-raclopride binding to dopamine D2 receptors. Farde, et al., 1989, *J. Cereb. Blood Flow Metab* 9:696-708. Briefly, specific binding to a receptor is a function of the density of receptors (Bmax) and the dissociation constant of the ligand (Kd). Specific binding of the ligand reaches a maximum during the time span of the imaging procedure. The time of maximal specific binding is determined from time activity curves (TAC) of specific and non-specific binding of the ligand. By assuming that non-specific binding is negligible in striatum and occipital cortex, the striatal time activity curve (StrTAC) represents the kinetic behavior of specifically bound plus free ligand, while the occipital cortex TAC (OccTAC) represents the kinetic behavior of only free ligand. Under these assumptions, the function, (StrTAC−OccTAC) defines the time dependence of bound ligand in the striatum. When this curve is fitted to a gamma variate function ($A^m e^{-mt}$), and the maximum is divided by the value of the occipital cortex TAC at the same time, an equilibrium estimate of (k3/k4) is obtained.

Reconstructed SPECT images were processed by the central reading facility. Transaxial images containing the striatum were summed at each time point using standardized criteria. Regions of interest (ROIs) were drawn around the left striatum, the right striatum, and a third ROI over the occipital cortex. TAC[1]s defined for average striatal and occipital cortex activity were used to calculate the striatal binding potential using the following formula:

$$k3/k4 = \text{Max}\{\text{StrTAC OccTAC}\}\text{Time} = t / \{(\text{OccTAC})\}\text{Time} = t$$

The Binding Potential (BP) data collected from 24 patients was analysed. The results are tabulated below.

TABLE 2

| | BP Uncorrected - Adjusted to age of 28.4 years | |
|---|---|---|
| | ALTROPANE ™ DIAGNOSIS | |
| Clinical Diagnosis | ADHD (BP ≧ 2.75) | Non-ADHD (BP < 2.75) |
| ADHD | 6 | 2 |
| Non-ADHD | 2 | 14 |

Sensitivity = 6/8 = 75%
Specificity = 14/16 = 87.5%
PPV = 6/8 = 75%
NPV = 14/16 = 87.5%

TABLE 3

BP Corrected - Adjusted to age of 28.4 years

| | ALTROPANE ™ DIAGNOSIS | |
|---|---|---|
| Clinical Diagnosis | ADHD (BP ≧ 2.90) | Non-ADHD (BP < 2.90) |
| ADHD | 6 | 2 |
| Non-ADHD | 2 | 14 |

Sensitivity = 6/8 = 75%
Specificity = 14/16 = 87.5%
PPV = 6/8 = 75%
NPV = 14/16 = 87.5%

TABLE 4

Corrected BP
No UCSD

| | Non-ADHD | ADHD |
|---|---|---|
| | 1.57 | 2.33 |
| | 2.03 | 2.67 |
| | 2.05 | 2.91 |
| | 2.05 | 2.97 |
| | 2.11 | 3.27 |
| | 2.12 | 3.32 |
| | 2.23 | 3.52 |
| | 2.34 | 3.64 |
| | 2.43 | |
| | 2.46 | |
| | 2.53 | |
| | 2.54 | |
| | 2.72 | |
| | 2.81 | |
| | 2.93 | |
| | 3.03 | |
| N | 16 | 8 |
| Average | 2.37 | 3.08 |
| Std Dev. | 0.39 | 0.44 |
| 95% CI | 0.19 | 0.31 |

T test, one tail unequal variance
P = 0.0011

($^{123}$I)-Altropane™ has been studied in several clinical trials in healthy volunteers, patients with Parkinson's Disease, patients with non-Parkinsonian movement disorders, and in adult patients with ADHD. ($^{123}$I)-Altropane™, at doses of 5-8 mCi, (8 mCi is equivalent to 14.4 ng, or 34 pmol Altropane™), has been used for the majority of studies. The injections have been well tolerated and no significant treatment associated adverse events have been reported among over 200 human subjects studied to date.

The above study with single photon emission computed tomography (SPECT) using ($^{123}$I)-Altropane™ demonstrates good correlation between increased striatal binding and the diagnosis of adult patients with ADHD. Thus, it appears that the methods of the present invention, e.g., using ($^{123}$I)-Altropane™ SPECT, can provide an independent and objective diagnostic test that will complement the clinical diagnosis of ADHD.

EXAMPLE 3

Participants 20 adults having ADHD and 20 age-matched healthy control volunteers were used in the study. The ADHD adults were from psychiatry outpatient clinics and were required to meet the following inclusion criteria: (1) meet full diagnostic criteria for both current and childhood ADHD using DSM-IV criteria (American Psychiatric Association: Diagnostic and Statistical Manual for Mental Disorders (4$^{th}$ ed.). Washington, DC, American Psychiatric Association, 1994) as assessed during a clinical interview employing a semi-structured interview form conducted by either a licensed clinical psychologist or psychiatrist; (2) absence of comorbid mood, oppositional defiant, conduct, and anxiety disorders and autism, or Tourette's syndrome; (3) no use of stimulant medication within the prior month; (4) no recent illicit drug use by history and by urine drug screen obtained during the initial evaluation; (5) absence of history of significant head injury involving loss of consciousness, thyroid abnormalities, seizures, or brain surgery; (6) a score <16 on the Hamilton Depression Scale (Hamilton M: A rating scale for depression. J Neurol Neurosurgical Psychiatry 1960; 23:56-62) and <19 on the Beck Depression Scale; (Hamilton M, The assessment of anxiety states by rating. Brit J Med Psychol 1959; 32:50-55) (7) a score <21 on the Hamilton Anxiety Scale; (Beck A, Ward C, Mendelson M: An inventory for measuring depression. Arch Gen Psychiatry 1961; 4:561-571) (8) age between 18 and 40 years; and (9) IQ score >75 as assessed by standardized intelligence testing.

Control volunteers were obtained from advertisements placed in the participating sites, regional newspapers, and known acquaintances of the investigators. These participants had to be of the same age as the ADHD adults and demonstrate an absence of ADHD currently and in childhood. This was established by having 3 or fewer inattention and 3 or fewer hyperactive-impulsive symptoms both currently and in childhood and by meeting no other criteria for ADHD from the DSM-IV as established by semi-structured interview (as above). All other exclusionary criteria noted for the ADHD group applied to this group as well. All female participants were required to have a negative urine pregnancy test taken on the day the scan was administered. Information from the participant selection criteria and demographic data is shown in Table 1.

TABLE 1

Demographic and initial subject selection information for each group

| | ADHD | | Control | | | |
|---|---|---|---|---|---|---|
| Measure | Mean | SD | Mean | SD | t | p< |
| Age (in years) | 28.4 | 5.6 | 28.2 | 6.3 | 0.10 | 0.92 |
| Reading (standard score) | 103.5 | 7.7 | 108.4 | 12.1 | 1.57 | 0.13 |
| Spelling (standard score) | 103.7 | 7.7 | 108.9 | 9.0 | 1.97 | 0.06 |
| Math (standard score) | 102.8 | 14.6 | 103.0 | 12.0 | 0.04 | 0.97 |
| # ADHD Symptoms (current) Inattention | 7.5 | 1.2 | 0.1 | 0.5 | 23.61 | <0.0001 |
| # ADHD Symptoms (current) Hyperactivity | 5.5 | 2.1 | 0.5 | 0.8 | 9.09 | <0.0001 |
| Beck Depression Scale (raw) | 7.5 | 4.3 | 1.0 | 2.1 | 5.61 | <0.0001 |
| Hamilton Anxiety Scale (raw) | 3.2 | 3.1 | 0.8 | 1.3 | 3.00 | 0.0070 |
| Hamilton Depression Scale (raw) | 3.0 | 3.2 | 1.2 | 2.0 | 2.03 | 0.0529 |

ADHD = attention deficit hyperactivity disorder;
SD = standard deviation;
t = results for the t-test;
p = probability value for the t-test if significant (p, .05).

Procedures

All participants were seen for three separate visits. During the first visit, written informed consent was obtained along with basic demographic data and medical/surgical history. The Structured Clinical Interview for DSM-IV disorders (SCID) (Spitzer R L, Williams J, Gibbon M, First M B: The Structured Clinical Interview for DSM-III-R (SCID). New York: Biometric Research Department, New York State Psychiatric Institute, 1989) and the module for the disruptive behavior disorders from the Kiddie-Schedule for Affective Disorders and Schizophrenia (K-SADS-E) (Orvaschel H, Puig-Antich J: Schedule for Affective Disorders and Schizophrenia for School-age Children: Epidemiologic $4^{th}$ Version. Ft. Lauderdale, Fla., Nova University Center for Psychological Study, 1987) were then conducted and the rating scales collected (e.g., Hamilton scales, Beck Depression Scale, and adult ADHD scales) (Barkley R A, Murphy K R: Attention Deficit Hyperactivity Disorder: A Clinical Workbook. New York, N.Y., Guilford Publications, 1998). Eligibility criteria were then reviewed and established. Several neuropsychological tests were given. Blood and urine samples were collected along with a 12-lead electrocardiogram. Participants were then given the SSKI or Lugol solution to ingest orally 24 hours before their next scheduled appointment for the SPECT scan. Some ADHD adults had been taken prescribed stimulants for management of their ADHD. With their physician's permission, these participants were removed from their medication for a four-week period prior to being scheduled for their SPECT scan.

During the second visit, scheduled for 1-5 weeks after the initial visit, the SPECT scan was conducted. Participants were evaluated at baseline for possible adverse events and all eligibility criteria were reviewed once again. All were then queried about their having taken the Lugol solution within the past 24 hours. Females then received a urine pregnancy test. Pre-injection vital signs and a brief neurological exam were conducted after which participants were positioned in the scanner. Over a 30 second period, the [$^{123}$I] altropane was infused intravenously. A series of two-minute serial SPECT scans were then obtained for 60 minutes after which vital signs were again tested, the 12-lead ECG obtained again, and the brief neurological exam was repeated.

A third clinical visit was scheduled the following day at which time participants were interviewed about possible adverse events, a physical exam was conducted, vital signs and the 12-lead ECG were repeated, and a blood sample obtained.

SPECT Scan

While positioned horizontally in the scanner and [$^{123}$I] altropane was injected. Serial two minute scans were acquired for a period of 60 minutes.

Time activity curves (TAC) in the striatal regions (STR) were compared with areas in the occipital cortex (OCC) to calculate the time dependence of bound [$^{123}$I] altropane STR minus OCC). These data were fit to a gamma variate function and divided by the maximum OCC TAC to determine an equilibrium estimate of DAT binding potential ($B_{max}/K_d$). Measures of binding potential were then standardized to age 28.4 years for comparison between the ADHD and control groups.

Results

Forty subjects enrolled in the study (20/group). SPECT data were successfully obtained from only 24 adults; 8 in the ADHD group and 16 in the control group. Excessive head motion occurred in 7 cases and unreconstructable scans occurred in another 9 cases such that 16 of the 40 original cases (12 ADHD and 4 controls) were eliminated from further analysis. The mean age-corrected binding potential for the ADHD group was 3.08 (SD=0.45, 95% CI=0.38) while that for the control group was 2.38 (SD=0.38, 95% CI=0.20). One-tailed t-test (unequal variance) revealed that the ADHD group had significantly greater binding potential for the [$^{123}$I] altropane than did the control group (p=0.0003). Regression analyses were conducted using the entire sample and predicting age-corrected altropane binding potential. The contribution of each of the following list of independent variables was examined separately: number of inattention symptoms, number of hyperactive-impulsive symptoms, reading, math, and spelling standard scores, Hamilton Depression Scale rating, Hamilton Anxiety Scale rating, and Beck Depression Scale rating. In the model for inattention and hyperactive-impulsive symptoms, age was included first. Then each variable was entered and the regression model analysis computed. For the remaining variables, both age and diagnostic category were entered first, followed by the independent variable. The partial R square that is reported represents the contribution the variable makes to the model, over and above age for the two ADHD symptom lists and age and diagnostic category for the remaining variables. The results were as follows: inattention: p=0.0008 (partial $R^2$=40.4%), hyperactivity: p=0.0014 (partial $R^2$=37.5%), reading: p=0.06 (partial $R^2$=9.51%), spelling: p=0.25 (partial $R^2$=3.74%), math: p=0.16 (partial $R^2$=5.43%), HAM-D: p=0.96 (partial $R^2$=0.00%), HAM-A: p=0.76 (partial $R^2$=0.27%), and Beck: p=0.31 (partial $R^2$=2.99%)). This series of analyses demonstrates that it is specifically inattention and hyperactivity that are substantially related to [$^{123}$I] altropane binding potentials and not other frequently comorbid symptoms.

To determine the classification accuracy of the age-corrected binding potentials, a BP cutoff score was selected as being +1 SD above the normal mean (2.76) for determination of ADHD diagnosis. Sensitivity was determined to be 75% (6/8) while specificity was found to be 87.5% (14/16). Positive predictive power was 75% (6/8) while negative predictive power was 87.5% (14/16).

The present results show increased dopamine transporter density in striatum in adults with ADHD relative to an age-matched control group. Adults with ADHD had 30 percent higher [$^{123}$I] altropane uptake in striatum than did control adults. Moreover, altropane binding potentials were significantly related to degree of both inattention and hyperactive-impulsive symptoms, further solidifying the conclusion that increased dopamine transporter density is associated with the degree of ADHD symptoms within this sample. Regression analyses also demonstrated that the comorbid levels of depression, anxiety, and academic learning abilities did not contribute significantly to these results once age and ADHD diagnosis were controlled.

The invention has been described in detail including preferred embodiments. However, it will be appreciated that those skilled in the art may make changes and improvements within the spirit and scope of this invention.

What is claimed is:

1. A method of determining the effectiveness of an ADHD treatment for a human patient, the method comprising:
   a) assessing an initial dopamine transporter level in at least one region of said patient's central nervous system;
   b) applying the ADHD treatment to the human patient;
   c) assessing a subsequent dopamine transporter level in said at least one region of said patient's central nervous system; and d) comparing the dopamine transporter level in step (a) with the dopamine transporter level in step (c), wherein a decrease in dopamine transporter levels indicates that the treatment is effective.

2. The method of claim 1, further comprising administering to the patient a labeled dopamine transporter ligand before at least one of the assessing steps, and wherein the assessing comprises determining the amount of labeled dopamine transporter ligand that is bound to dopamine transporter.

3. The method of claim 2, wherein the dopamine transporter ligand comprises a compound that binds to the dopamine transporter.

4. The method of claim 1, wherein the second assessing step occurs two weeks or more after the applying step.

5. The method of claim 1, wherein the treatment comprises a pharmaceutical treatment.

6. The method of claim 1, wherein the pharmaceutical treatment comprises administration of a pharmaceutical selected from the group consisting of methylphenidate, pemoline, and an amphetamine.

7. The method of claim 1, wherein the assessing step comprises PET or SPECT imaging.

8. The method of claim 1, further comprising administering to the patient a labeled dopamine transporter ligand before at least one of the assessing steps, the assessing steps comprise assessing dopamine transporter availability, and the comparing step comprises comparing dopamine transporter availability in step (a) with the dopamine transporter availability in step (c), wherein a lower dopamine transporter availability in step (c) indicates that the treatment is effective.

9. The method of claim 1, further comprising administering to the patient a labeled dopamine transporter ligand before at least one of the assessing steps, the assessing steps comprise assessing dopamine transporter binding potential, and the comparing step comprises comparing dopamine transporter binding potential in step (a) with the dopamine transporter binding potential in step (c), wherein a lower dopamine transporter binding potential in step (c) indicates that the treatment is effective.

10. A method of monitoring the progress of a treatment for ADHD in a human patient, the method comprising:
   assessing dopamine transporter level in at least one region of said patient's central nervous system a plurality of times during said treatment for ADHD to obtain a plurality of dopamine transporter level assessments; and
   comparing at least two of the dopamine transporter level assessments, such that progress of the treatment for ADHD is monitored.

11. The method of claim 10, further comprising administering to the patient a labeled dopamine transporter ligand before the assessing step, and wherein the assessing comprises determining the amount of labeled dopamine transporter ligand that is bound to dopamine transporter.

12. The method of claim 11, wherein the dopamine transporter ligand comprises a compound that binds to the dopamine transporter.

13. The method of claim 10, wherein the treatment comprises a pharmaceutical treatment.

14. The method of claim 13, wherein the pharmaceutical treatment comprises administration of a pharmaceutical selected from the group consisting of methylphenidate, pemoline, and an amphetamine.

15. The method of claim 14, wherein the assessing step comprises PET or SPECT imaging.

* * * * *